US 6,777,584 B2
Aug. 17, 2004

(54) SELECTIVE COUPLING OF TERMINAL OLEFINS WITH ETHYLENE TO MANUFACTURE LINEAR α-OLEFINS

(75) Inventors: Abhimanyu Onkar Patil, Westfield, NJ (US); Stephen Zushma, Clinton, NJ (US); Timothy Daniel Shaffer, Hackettstown, NJ (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 119 days.

(21) Appl. No.: 10/081,321

(22) Filed: Feb. 22, 2002

(65) Prior Publication Data

US 2003/0166985 A1 Sep. 4, 2003

(51) Int. Cl.[7] ............................. C07C 2/30; C07C 2/34
(52) U.S. Cl. ..................... 585/511; 585/512; 585/513
(58) Field of Search ............................. 585/511, 512, 585/513

(56) References Cited

U.S. PATENT DOCUMENTS

| | | | |
|---|---|---|---|
| 3,558,738 A | * | 1/1971 | Dunn .......................... 585/513 |
| 3,652,687 A | | 3/1972 | Bergem et al. ...... 260/683.15 D |
| 3,655,810 A | | 4/1972 | Chauvin et al. ..... 260/683.15 D |
| 3,658,931 A | | 4/1972 | Crain et al. ............... 260/683 D |
| 3,689,587 A | | 9/1972 | Grebbell et al. .... 260/683.15 E |

FOREIGN PATENT DOCUMENTS

| | | | |
|---|---|---|---|
| BE | 622435 | 3/1963 | |
| EP | 0526943 A1 | 2/1993 | ............. C07C/2/34 |

* cited by examiner

Primary Examiner—Thuan D. Dang
(74) Attorney, Agent, or Firm—Estelle C. Bakun; Joseph C. Wang (57) ABSTRACT

A process for producing a linear α-olefin which comprises: reacting a stoichiometric excess of a terminal $C_n$ olefin with ethylene in the presence of an organometallic catalyst to produce a $C_{n+2}$ linear α-olefin, wherein the catalyst is capable of producing a Schulz-Flory distribution of the linear α-olefin with a Schulz-Flory constant of less than about 0.8 and wherein n is an integer between about 3 to 20.

24 Claims, 3 Drawing Sheets

SELECTIVE COUPLING OF TERMINAL OLEFINS WITH ETHYLENE TO MANUFACTURE LINEAR α-OLEFINS

The present invention generally relates to a novel process for selective coupling of terminal olefins with ethylene to manufacture linear α-olefins in the presence of organometallic coupling catalysts.

BACKGROUND OF THE INVENTION

Linear α-olefins are versatile intermediates and building blocks for the chemical industry. Their main applications are as comonomers for polyethylene ($C_4$–$C_8$), feedstock for surfactants ($C_{12}$–$C_{20}$), and plasticizers ($C_6$–$C_{10}$). Hydrocarboxylation of the $C_6$–$C_8$ α-olefins with cobalt-carbonyl/pyridine catalysts gives predominantly linear carboxylic acids. The acids and their esters are used as additives for lubricants. The $C_6$–$C_{10}$ α-olefins are hydroformylated to odd-numbered, linear primary alcohols, which are converted to surfactants or to polyvinyl chloride (PVC) plasticizers with phthalic anhydride. Oligomerization of (preferably) 1-decene using $BF_3$ catalysts gives oligomers that are used as synthetic lubricants, which are known as poly-α-olefins (PAO) or synthetic hydrocarbons. The $C_{10}$–$C_{12}$ α-olefins can be epoxidized by peracids; this opens up a route to bifunctional derivatives or ethoxylates as nonionic surfactants.

α-Olefins are produced worldwide at a rate of ca. $4\times10^9$ lb/year, predominantly through oligomerization of ethylene because of the high product quality and the good availability of ethylene. [Vogt, D. In *Applied Homogeneous Catalysis with Organometallic Compounds*; Cornils, B., Herrmann, W. A., Eds: VCH Publishers: 1996; Vol. 1: pp 245–256. (b) Parshall, G. W.; Ittel, S. D. In *Homogeneous Catalysis: The Applications and Chemistry of Catalysis by Soluble Transition Metal Complexes*; John Wiley & Sons: New York, 1992; pp 68–72. (c) Skupinska, *J. Chem. Rev.* 1991, 91, 613]. Current industrial commercial processes give α-olefins with a Schulz-Flory distribution, wherein the S-F constant is calculated from the ratio $C_{n+2}$ to $C_n$ compounds in the product mixture, also known as the chain growth factor (α). Other routes to α-olefins in decreasing importance are paraffin wax cracking, paraffin dehydrogenation, and alcohol dehydration.

The wide application and increasing need for α-olefins, as comonomers for polyolefins will cause the linear olefin market to grow. Linear α-olefins are very versatile intermediates and building blocks for the chemical industry. The lower $C_4$–$C_8$ α-olefins are mainly used as comonomers for polyethylene. Small amounts of up to 3% α-olefins are used to produce high-density polyethylene (HDPE) with a higher environmental stress/crack resistance and a slightly reduced density (0.959–0.938 g/cm³) compared with the homopolymer (0.965–0.955 g/cm³). Higher quantities of 4–12% α-olefins are added to produce linear low density polyethylene (LLDPE) with considerably reduced density (0.935–0.915 g/cm³), for which 1-butene and 1-hexene are preferred in the gas-phase process and 1-octene in the liquid phase. [Vogt, D. *Applied Homogeneous Catalysis with Organometallic Compounds*. Cornils, B.; Herrmann, W. A. Eds. VCH Publications, New York. 1996, p. 220.]

Other applications for α-olefins include feedstocks for surfactants ($C_{12}$–$C_{20}$) and plasticizers ($C_6$–$C_{10}$). Hydrocarboxylation of the $C_6$–$C_8$ α-olefins with cobalt carbonyl/pyridine catalysts gives predominantly linear carboxylic acids. The acids and their esters are used as additives for lubricants. The $C_6$–$C_{10}$ α-olefins are hydroformylated to odd-numbered linear primary alcohols, which are converted to polyvinyl chloride (PVC) plasticizers with phthalic anhydride. Oligomerization of (preferably) 1-decene, applying $BF_3$ catalysts, gives oligomers used as synthetic lubricants known as poly-α-olefins (PAO) or synthetic hydrocarbons. The $C_{10}$–$C_{12}$ α-olefins can be epoxidized by peracids; this opens up a route to bifunctional derivatives or ethoxylates as nonionic surfactants. Two basic reactions are commercially used to produce α-olefins. The first is based on the Aufbau reaction which oliogmerizes ethylene by the action of a trialkylaluminum. Two variations are practiced commercially. The first variation is a two-step process in which the chain-growth reaction is first accomplished at about 100° C. and 10 MPa ethylene pressure. In the following high-temperature elimination step, the α-olefins are displaced by ethylene at about 300° C. and 1 MPa. In this stoichiometric reaction sequence, a Poisson distribution of α-olefin products is obtained. The main disadvantage of this process is the large amount of aluminum alkyls needed in an industrial plant. To overcome this drawback, the following processes were developed.

An alternative process based on the Aufbau principle uses a one-step catalytic procedure, where chain growth and elimination occur simultaneously in the same reactor. About 0.4% wt. of $AlEt_3$ (with respect to ethylene reacted) is needed. For this process solvent heptane is used, at about 200° C. and 25 MPa ethylene pressure. After the reaction, the catalyst is destroyed by hydrolysis. In this catalytic reaction, a Schulz-Flory distribution of α-olefin is obtained.

A variation of this second method is based on a combination of stoichiometric and catalytic chain-growth reactions. Unifying these two parts with a transalkylation step allows very efficient control of the α-olefin chain lengths. The first oligomerization step uses a catalytic one-step process similar to the first process. The process is operated at 160–275° C. and 13–27 MPa of ethylene pressure. After the reaction, the catalyst is destroyed by hydrolysis.

The product mixture, consisting mainly of $C_4$–$C_{10}$ α-olefins, is distilled and separated into the $C_4$–$C_{10}$ and $C_{12}$–$C_{18}$ fractions. The latter can be used directly. The lower α-olefins are subjected to transalkylation with higher aluminum alkyls, liberating the higher α-olefins. The higher aluminum alkyls are produced in the stoichiometric part of the reaction, operating at about 100° C. and 20 MPa. In the second distillation, the liberated olefins are separated from the aluminum alkyls. These alkyls are fed into a chain-growth reactor, where they are grown with ethylene to long-chain aluminum alkyls, which are recycled to the transalkylation stage. Because of the recycle, co-oligomerization of product α-olefins with ethylene yields considerable amounts of branched olefins. The higher molecular weight $C_6$–$C_{18}$ fraction, especially, consists of only 63% linear α-olefins. The problem associated with both of the aforementioned processes is that they are done under stoichoimetric conditions and exhibit very low yields of α-olefins.

Another commercially available process is based upon the second basic reaction and produces poly-α-olefins by the oligomerization of ethylene. This process is known as the Shell Higher Olefin Process (SHOP). Catalysts used in this process are neutral Ni(II) complexes bearing bidentate monoanionic ligands [(a) Peuckert, M.; Keim, W. *Organometallics* 1983, 2, 594. (b) Keim, W.; Behr, A.; Limbacker, B.; Kruger, C. *Angew. Chem. Int. Ed. Engl.* 1983, 22, 503. (c) Keim, W.; Behr. A.; Kraus, G. *J. Organomet. Chem.* 1983, 251, 377. (d) Peuckert, M.; Keim, W. *J. Mol. Catal.*

1984, 22, 289. (e) Keim, W.; Schulz, R. P. *J. Mol. Catal.* 1994, 92, 21]. This ethylene oligomerization process combines oligomerization of ethylene, isomerization of the higher α-olefin products and the metathesis of these internal olefins with butenes or ethylene. It was designed to meet the market need for linear α-olefins for detergents. The nickel catalyst is prepared in situ from a nickel salt, e.g., nickel chloride, and a chelating phosphorus oxygen ligand like o-diphenylphosphinobenzoic acid. The nickel catalyst oligomerizes ethylene in toluene at 80° C. and 5 MPa to 99% linear olefins with 98% α-olefins. The α-olefins produced have a Schulz-Flory type of distribution over the whole range from $C_4$–$C_{30}^+$.

Problems associated with the aforementioned ethylene oligomerization process are that ethylene is a very expensive feed material and that the resultant α-olefins (i.e., $C_4$–$C_{30}^+$) have to be fractionated to yield the desired carbon numbered linear α-olefins. Another problem associated with such oligomerization is that undesirable branching and multiple isomeric olefins often result, thereby requiring a separate fractionation step which is both expensive and results in substantially lower selectivity yields of the desired linear α-olefin.

SUMMARY OF THE INVENTION

The present inventors have unexpectedly discovered a novel catalytic process for selective "coupling" of terminal olefins with ethylene to manufacture linear α-olefins in high yields with respect to ethylene and selectivity without the need for fractionation as discussed above. The unique process according to the present invention permits the 'designing' of a single carbon number linear α-olefin, while using, in part, less costly raw materials than expensive ethylene. This unique catalysis process can be used to make $C_6$–$C_{10}$ olefins by sequential coupling reactions using an α-olefin and ethylene, provided that the α-olefin is not ethylene, thereby avoiding the need to fractionate larger α-olefins, as required in the ethylene oligomerization process.

The present invention also provides many additional advantages which shall become apparent as described below.

A unique catalytic process for selectively coupling α-olefins (e.g., propylene, 1-butene, 1-pentene, 1-hexene, 1-heptene and 1-octene) with ethylene, wherein the α-olefins are used with ethylene so as to produce the desired linear $C_6$–$C_{10}$ α-olefins in high yield. The catalytic process according to the present invention provides for a unique method for converting α-olefins having a carbon number of, for example, $C_n$, to linear α-olefins having a carbon number of $C_{n+2}$, wherein n is an integer from about 3 to about 20. For example, this process provides for the coupling of: 1-butene with ethylene to produce 1-hexene, or 1-hexene with ethylene to produce 1-octene, or 1-octene with ethylene to produce 1-decene. The present invention utilizes a unique organometallic catalyst that is capable of producing: (a) a $C_{n+2}$ linear α-olefin from ethylene and a $C_n$ α-olefin; and/or (b) α-olefin products wherein every product contains at least one $C_n$ fragment stemming from a reactor $C_n$ reactor feed.

In general, the process for producing a linear α-olefin according to the present invention comprises: reacting a feed comprising a stoichiometric excess of a terminal $C_n$ olefin with ethylene in the presence of an organometallic catalyst to produce a $C_{n+2}$ linear α-olefin, wherein said catalyst is capable of producing a Schulz-Flory distribution of less than about 0.8 as observed for ethylene oligomerization and wherein n is an integer between about 3 to 20.

The terminal olefin is preferably selected from the group consisting of $C_3$ to $C_{20}$ olefins, e.g., propylene, 1-butene, 1-pentene, 1-hexene, 1-heptene and 1-octene and mixtures thereof, such that the product linear α-olefin is selected from the group consisting of: $C_5$ to $C_{22}$ linear α-olefins, preferably $C_6$–$C_{10}$ linear α-olefins. Preferably, a feed containing a mixture of three or less terminal olefins will be utilized, more preferably, a feed containing a single olefin will be utilized.

The coupling step is preferably conducted at a temperature in the range from about −100 to about 250° C., more preferably between about room temperature to about 100° C. The pressure during the coupling step is conducted at a pressure from about 0 to about 30,000 psig, preferably between about 0 to about 10,000 psig, most preferably between about 5 to about 3,000 psig.

The terminal olefin to ethylene typically has a molar ratio in the range between about 2:1 to about 1,000:1, preferably between about 10:1 to about 100:1.

The reaction step is preferably a catalytic coupling of said terminal olefin and said ethylene to form said linear α-olefin. It is also preferred that the reaction step be performed in the presence of a solvent. The solvent is preferably at least one solvent selected from the group consisting of: ethane, propane, butane, pentane, hexane, toluene, cyclohexane, cyclopentane, tetralin, methylene chloride, chlorobenzene, chloroform, o-dichlorobenzene, carbon dioxide and mixtures thereof.

The catalyst is preferably a transition metal-based catalyst selected from the group consisting of: Group 6 metals, Group 8 metals, Group 9 metals, Group 10 metals, Group 11 metals (IUPAC) or mixtures thereof. The transition metal-based catalyst is typically at least one selected from the group consisting of: chromium trimerization catalysts, Brookhart type transition metal catalysts, iron or cobalt catalysts, pseudotetrahedral nickel complex catalysts, sulfur-containing nickel complexes and SHOP catalysts. The term "pseudotetrahedral" is used herein to describe the geometric structure of the metal complex, it does not exclude a pure "tetrahedral" geometrical arrangement. A more detailed description of pseudotetrahedral can be found in U.S. Pat. No. 6,180,788 herein incorporated by reference.

The process according to the present invention is either a continuous, semi-continuous or batch type process.

Finally, the linear $C_{n+2}$ α-olefin of the present invention is formed from the reaction product of a stoichiometric excess of a terminal $C_n$ olefin with ethylene in the presence of an organometallic catalyst.

Other and further objects, advantages and features of the present invention will be understood by reference to the following specification in conjunction with the annexed drawings, wherein like parts have been given like numbers.

DESCRIPTION OF THE PREFERRED EMBODIMENTS

The present invention provides a method for producing linear α-olefins by contacting ethylene with α-olefins, such as propylene, 1-butene, 1-pentene, 1-hexene, 1-heptene, 1-octene or 1-decene, under certain temperature and pressure conditions conducive to forming coupled products while minimizing or totally eliminating, any polymer or ethylene-only containing coproduct. Generally, in this process α-olefins, such as as propylene, 1-butene, 1-pentene, 1-hexene, 1-heptene, 1-octene or 1-decene, are used in excess compared to ethylene. The mole ratio of α-olefins, such as 1-butene, 1-hexene, 1-octene or 1-decene, to ethylene is typically from about 2:1 to about 1000:1, preferably about 10:1 to about 100:1.

The process for coupling α-olefins and ethylene according to the present invention in order to yield desired linear α-olefins in one step is conducted at a temperature in the range from about −100 to about 250° C., more preferably between about room temperature to about 100° C., and at pressures from about 0 to about 30000 psig, more preferably between about 0 to about 10,000 psig, most preferably between about 5 to about 3000 psig.

Furthermore, catalytic coupling according to the present invention may take place in a solvent, neat (e.g., no solvent and liquid condensed olefin), or in a gas phase (e.g., olefin in gas phase and catalyst in the solid phase). When coupling is conducted in a solvent phase, suitable solvents include, but are not limited to ethane, propane, butane, pentane, hexane, toluene, cyclohexane, cyclopentane, tetralin, methylene chloride, chlorobenzene, chloroform, o-dichlorobenzene, carbon dioxide and mixtures thereof.

Coupling in the gas phase requires a solid catalyst or a catalyst on a solid support. Supported catalysts have been described in Exxon Chemical's gas phase catalyst technology as described in U.S. Pat. No. 5,554,704 which is herein incorporated by reference. U.S. Pat. No. 5,554,704 teaches a process for producing a supported catalyst. The supported catalyst can then be used in a solvent free system wherein gas phase α-olefin and ethylene are passed through a fixed bed of catalyst. The condensed α-olefin product is then separated from the system.

The process of the instant invention can be carried out in a continuous, semi-continuous or batch manner. The continuous process involves the continuous addition of reactants and catalyst components to the reactor with simultaneous removal of the product. For a gas phase process, the catalyst may be charged to the reactor prior to the introduction of the reactants and removal of the products. Alternatively, the α-olefin, solvent and catalyst components can be charged to the reactor with ethylene semi-continuously added to the reactor as it is consumed. Conversely, in a batch process, all the components of the reaction are charged to the reactor and reacted until the complete consumption of the limiting reagent (i.e., ethylene).

Catalysts useful in the present invention preferably exhibit an S-F (Schulz-Flory) constant of less than about 0.8 as observed for ethylene oligomerization, wherein the S-F constant is calculated from the ratio $C_{n+2}$ to $C_n$ compounds in the product mixture, also known as the chain growth factor (α). More preferably, selected catalysts exhibit an S-F constant of less than about 0.65 with those catalysts exhibiting an S-F constant of about 0.5 or less being most preferred.

In general, suitable catalysts that exhibit these characteristics comprise:
1) a transition metal compound wherein the transition metal is a Group 6, 8, 9, 10 or 11 metal or mixtures thereof;
2) in the event that the transition metal compound is not in the oxidation state of zero or that it possess a monoanionic ligand selected from the group consisting of: hydride, substituted or unsubstituted $C_1$ to $C_{30}$ hydrocarbyl, alkoxide, aryloxide, amide, halide, phosphide, or Group 14 metalloids, an activator (also referred to as a co-catalyst) is preferably added to generate the active transition metal/activator complex, said activator being in amounts sufficient to activate the transition metal compound. The activator is typically present in a stoichiometric amount up to 10,000:1 activator:transition metal complex.

The strong propensity of transition metal-based catalysts to undergo α-hydrogen elimination reactions has largely relegated this class of catalysts to applications in dimerization and oligomerization processes. Some of these catalysts and processes are discussed below:

Chromium trimerization catalyst

Brookhart type Ni and Pd catalysts

Pyridine bisimine Fe or Co complexes

Ni-BBIM catalysts

Ni-thiolene catalysts

Shell Higher Olefin Process (SHOP) catalysts

Illustrative, though not limiting examples of suitable catalysts include those described below.

Chromium Trimerization Catalyst

May include chromium complexes as disclosed in U.S. Pat. No. 4,668,838; U.S. Pat. No. 5,814,575 and U.S. Pat. No. 4,777,315 (which are incorporated herein by reference), which comprise a mixture of a chromium compound, an aluminoxane and a third component selected from hydrocarbyl isonitriles, amines and ethers. Still other catalysts may comprise a mixture of MAO, polydentate phosphine and chromium salt. Other catalysts, such as, triazacyclohexane complexes of chromium catalyst as disclosed in Kohn, R. D. et al. Angew. Chem. Int. Ed. 2000, 39, 4337 (incorporated herein by reference), are also useful in the process according to the present invention.

M (II) α-diimine Complexes ("Brookhart" type Ni Catalysts)

Brookhart type metal catalysts include cationic Ni(II) and Pd(II) α-diimine complexes. In the above formula M is either Ni or Pd and each R is independently selected from hydrogen, halogen, hydrocarbyl, substituted hydrocarbyl, heterohydrocarbyl, and substituted heterohydrocarbyl. When diimine ligands lacking bulky aryl ortho substituents are used, the resulting Ni(II)-based systems produce a Schulz-Flory distribution of ethylene oligomers. Treatment of the Ni(II) dibromide complexes with MAO, modified MAO (methyl isobutyl aluminoxane), or aluminum alkyl activators, such as, $Et_2AlCl$ in toluene generates active cationic catalysts that oligomerize ethylene to produce a Schulz-Flory distribution of linear α-olefins. Reaction conditions can be adjusted within the noted parameters to yield selectivity as high as 96% for linear α-olefins. Catalysts which exhibit these features are described in U.S. Pat. Nos. 5,880,323, 6,034,259 and U.S. patent application Ser. No. 08/590,650, all incorporated by reference herein.

Pyridine Bisimine Fe or Co Complexes:

Fe (II) or Co (II)-pyridine bisimine complexes can also be used as oligomerization catalysts according to the present invention. In the above foemula M is either Fe or Co and each of $R_1$, $R_2$, and $R_3$ is independently selected from hydrogen, halogen, hydrocarbyl, substituted hydrocarbyl, heterohydrocarbyl, and substituted heterohydrocarbyl. As observed for the α-diimine-based nickel and palladium catalysts, the bulk around the metal center is a key in retarding chain transfer to obtain a high molecular weight polymer. Accordingly, as ligand bulk is reduced by varying the ortho substituents on the imine aryl and by using formylpyridine instead of acetylpyridine, a favorable shift to ethylene oligomers occurs. By reducing the steric bulk of these pyridinebisimine ligands the resultant iron catalysts oligomerize ethylene to linear α-olefins with remarkably high activity and selectivity. Catalysts with these features are disclosed in WO 99/02472, WO 00/58320, WO 00/69869, and WO 00/73249 (which are incorporated herein by reference). Catalyst have also appeared in Small, B. L. et. al. J. Amer. Chem. Soc. 1998, 120, 7143 and Britovsek, G. J. P. et. al. Chem. Commun. 1998, 849 (incorporated herein by reference), are also useful in the process according to the present invention. The turnover frequencies are dependent on catalyst structure, ethylene pressure, and temperature.

Ni-BBIM Catalysts

Ni-BBIM catalyst complexes, when used with an activating cocatalyst, provides a catalyst composition, which is useful herein for the coupling of α-olefins with ethylene in accordance with the present invention.

The Ni-BBIM catalyst complexes are formed by the reaction of a group ten metal salt, preferably a nickel metal salt and a nitrogen ligand having a monodentate, bidentate, tridentate, or multidentate nitrogen ligand and activating cocatalyst such as methyl alumoxane (a.k.a., "MAO").

The composition of this catalyst is preferably a transition metal complex having the formula $LMiX(X')_n$ wherein n equals 0 or 1. X and X' are independently selected from the group consisting of halides, hydride, triflate, acetates, borates, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolates, carbon monoxide, cyanate, olefins including diolefins and cycloolefins, and any other moiety into which a monomer can insert. L is a nitrogen-containing monodentate, bidentate, tridentate or multidentate ligand having two or more nitrogen atoms, and M is nickel, palladium or platinum.

Preferably, X and X' are independently selected from the group consisting chloride and bromide. More preferrably, X equals X'.

Hence, in a preferred catalyst complex, L may have the formula $A(ZR^*)_mA'$ or AA' wherein A and A' are amine segments independently selected from the group consisting of:

wherein R1 is independently selected from the group consisting of hydrogen, $C_1$ through $C_{12}$ alkyl, $C_3$ through $C_{12}$ cycloalkyl, aryl, and trifluoroethyl; R2 and R3 are independently selected from the group consisting of hydrogen, $C_1$ through $C_{12}$ alkyl, $C_3$ through $C_{12}$ cycloalkyl, $C_1$ through $C_{12}$ alkoxy, F, Cl, $SO_3$, $C_1$ through $C_{12}$ perfluoroalkyl, trimethylsilyl, and $N(CH_3)_2$. Z is carbon and R* is independently selected from the group consisting of hydrogen, $C_1$ through $C_{12}$ alkyl, $C_3$ through $C_{12}$ cyclo alkyl, aryl, $C_1$ through $C_{12}$ alkoxy, F, Cl, $SO_3$, $C_1$ through $C_{12}$ perfluoroalkyl, trimethylsilyl, and $N(CH_3)_2$. Finally, m equals an integer from 1 to 22, preferably, m equals 1 to 12.

Among the various nitrogen ligands, the following ligands are particularly preferred: 1,1'-bis(1-methylbenzimidazol-2-yl)-1"-methoxymethane; 1,1'-bis(1-butylbenzimidazol-2yl) pentane; and 2,2'-bis(2-(1-ethylbenzimidazol-2-yl))biphenyl 2,6-di-tert-butylpyridine, 2,2'-bipyridine, 4,4'-dimethyl-2,2'-bipyridyl, 4,4'-dimethyl-2,2'-bipyridyl, 5,5'-dimethyl-2,2'-bipyridyl, 6,6'-tert-butyl-2,2'-dipyridyl, 4,4'-diphenyl-2,2'-bipyridyl, 1,10-phenanthroline, 2,7-dimethyl-1,10-phenanthroline, 5,6-dimethyl-1,10-phenanthroline, 4,7-diphenyl-1,10-phenanthroline and 2,9-dimetyl-5,7-diphenyl-1,10-phenanthroline, 1,1'-bis(1-methylbenzimidazol-2-yl)-1"-methoxyethane, 3,3'-(1-ethylbenzimidazol-2-yl)-pentane, 2,2'-bis{2-(1-alkylbenzimidazol-2-yl)}biphenyl, 2,2'-bis(1-octylbenzimidazole-2yl)biphenyl, and 3,3'-bis(1-butylbenzimidazol-2yl)1"-pentane, ethylenediamine, 2,2'-bipiperidine, N,N,N',N'-tetramethylethylenediamine, N,N,N',N'-tetraethylethylenediamine, N,N,N',N'-tetraethyl-1,3-propanediamine, N,N'-di-tert-butylethylenediamine, N,N'-dibutyl-1,6-hexanediamine, N,N-dibutyl-1,3-propanediamine, N,N'-diethylethylenediamine, N,N'-diphenylethylenediamine and 1,4-diazabicyclo[2,2,2]octane and mixtures thereof.

The 1,1'-bis(1-methylbenzimidazol-2-yl)-1"-methoxymethane ligand has the following structure:

The 1,1'-bis(1-butylbenzimidazol-2yl) pentane ligand has the following structure:

The 2,2'-bis(2-(1-ethylbenzimidazol-2-yl))biphenyl ligand has the following structure:

The catalyst may also be the reaction product of the composition having the formula LMX(X')n, as defined above, and an activating cocatalyst. The activating cocatalyst may be selected from the group consisting of alkylalumoxanes, aluminum alkyls, aluminum halides, alkyl aluminum halides, Lewis acids, alkylating agents, and mixtures thereof. More preferably, the activating cocatalyst is methyl alumoxane.

Lewis acids other than any of the foregoing list and the mixtures of the foregoing can also be used in conjunction with alkylating agents, such as methyl magnesium chloride and methyl lithium. Examples of such Lewis acids are those compounds corresponding to the formula: $R''''_3B$, where each R'''' is independently selected from hydrogen, silyl, hydrocarbyl, halohydrocarbyl, alkoxide, aryloxide, amide or combination thereof, said R'''' having up to 30 nonhydrogen atoms.

It is to be appreciated by those skilled in the art, that the above formula for the preferred Lewis acids represents an empirical formula, and that many Lewis acids exist as dimers or higher oligomers in solution or in the solid state. Other Lewis acids which are useful in the catalyst compositions of this invention will be apparent to those skilled in the art.

The composition described above may also be supported. The support material is preferably a porous material which includes, but is not limited to, inorganic oxides, talc, and inorganic chlorides. The support material may also be resinous materials such as polystyrene polyolefin or polymeric compounds. The support material may also be any other organic material that has an average particle size greater than approximately 10 micron. These catalysts are generally physisorbed on the support. The catalysts can also be supported on mesoporous materials. Preferably, the catalyst complex is supported by silica. To prepare a supported catalyst, the skilled artisan can employ known techniques. For example, catalyst slurry in solvent such as toluene can be prepared by mixing the catalyst with solvent. Activator like MAO can then be added to obtain a suspension. The support material such as silica can then be added. The mixture is typically stirred at room temperature for 1 hour and the solvent evaporated under high vacuum to isolate powder. The supported material can then be used to do coupling reactions.

Other examples of suitable activators are discussed in U.S. Pat. Nos. 6,037,297 and 5,198,401 to Stibrany et al.; U.S. Pat. No. 5,198,401, and PCT Application Serial Nos. PCT/US97/10418 and PCT/US96/09764, all incorporated by reference herein.

Ni-thiolene Catalysts

A variety of Ni-thiolene catalysts can be used to catalyze the α-olefin and ethylene coupling taught herein. For example, in the presence of MAO, nickel complexes, such as, nickel dithiocarbamate, nickel dithiolene, and nickel 1,3-dithioketonate complexes efficiently catalyze the coupling of α-olefins and ethylene. The catalyst preparation is described in co-pending and commonly owned U.S. patent application Ser. No. 10/021976 filed Oct. 30, 2000, entitled "Method for oligomerizing olefins to form higher olefins using sulfur-containing and sulfur-tolerant catalysts, which is incorporated herein by reference. These catalysts show some degree of tolerance to sulfur-containing contaminants. For example, the catalytic activity of nickel bis (1,2-diphenylethylene-1,2-dithiolate), e.g., $Ni(S_2C_2Ph_2)_2$ is only slightly inhibited by n-propyl mercaptan and thiophene. The sulfur-tolerant feature of these sulfur-containing catalysts presents potentially significant advantages over other reported catalysts that are poisoned by sulfur in the olefin stream thus requiring expensive feed clean-up. Some examples of nickel complexes include nickel dithiolene and nickel dithiocarbamate complexes, $Ni(S_2C_2Ph_2)_2$, $Ni[S_2C_2(CF_3)_2]_2$, $Ni(S_2CNBu_2)_2$, and $Ni(S_2CNBu_2)(PPh_3)Cl$.

The Ni-thiolene catalyst composition may comprise an activating co-catalyst and a compound having the formula $M[S_2C_2(R^aR^b)]_2$ or $M[S_2C_6(R^1R^2R^3R^4)]_2$, wherein M is a transition metal, $R^a$, $R^b$, $R^1$, $R^2$, $R^3$ and $R^4$ may be the same or different and are are independently selected from the group consisting of hydrogen, electron withdrawing groups and unsubstituted and substituted hydrocarbyl groups; and an activating cocatalyst. Such compounds having formulas (I) $M[S_2C_2(R^aR^b)]_2$ and (II) $M[S_2C_6(R^1R^2R^3R^4)]_2$ are known in the art as metal dithiolene compounds. Dithiolene is a commonly used name for 1,2-enedithiolate or benzene-1,2-dithiolate and related dithiolates.

Compounds of formula (I) and (II) may be obtained by reacting a suitable source of metal with a suitable source of ligand, which may be obtained from commercial sources or prepared as described according to methods known in the art. The source of metal can also be obtained commercially. Typical examples of how to make the dithiolene compounds of formula (I) can be found in the literature, as disclosed in Schrauzer, et al., J.A.C.S., Vol. 87 (7), 1483–9 (1965), incorporated by reference herein. Anions of compounds of formula (II) can be made by reacting a metal salt with arene-1,2-dithiols and their analogs, as taught in Gray, et al., J.A.C.S., Vol. 88 (21), 4870–5 (1966), incorporated by reference herein. The neutral form of formula (II) is accessible by oxidation, either chemically or electrochemically. Additionally, compounds of formula (I) may be produced by the processes taught in U.S. Pat. No. 6,120,692 to Wang, et al., and Davison, et al., Inorganic Syntheses, Vol. 10, 8–26 (1967), both incorporated by reference herein.

M[S₂C₂(RᵃRᵇ)]₂ (I)

M[S₂C₆(R¹R²R³R⁴)]₂ (II)

The structural formula for the transition metal bis (dithiolene) compounds are shown above in Formula (I) for M[S₂C₂(RᵃRᵇ)]₂ and in Formula (II) for M[S₂C₆ (R¹R²R³R⁴)]₂. In formula (I), M is a transition metal, preferably either Fe, Co, Ni, Pd or Pt. Most preferably, M is Ni. $R^a$ and $R^b$ may be the same or different, and are independently selected from hydrogen, electron-withdrawing groups including those that are or contain heterocyclic, cyano, carboxylate, carboxylic ester, keto, nitro, and sulfonyl groups, and hydrocarbyl groups, including unsubstituted, fully substituted, and partially substituted alkyl, cyclo alkyl, alkenyl and aryl groups. Preferably, $R^a$ and $R^b$ will be electron-withdrawing groups, more preferably, cyano groups or halo substituted groups, even more preferably, halo substituents such as fluoro groups and most preferably, $R^a$ and $R^b$ will be $CF_3$ or CN.

Another type of Ni-thiolene catalyst complex is a dithiolene compound that contains benzene dithiolato ligands, represented by the structure in formula (II) above. In the formula (II), M also is a transition metal with the same characteristics as described for formula (I). $R^1$, $R^2$, $R^3$, and $R^4$ my be the same or different and are each independently selected from hydrogen, electron-withdrawing groups as described above, and unsubstituted or fully or partly substituted hydrocarbyl groups including alkyl, cycloalkyl, alkenyl, and aryl groups, preferably with substituents at the carbon atoms of the hydrocarbyl group that are electron-withdrawing groups. Preferably, the group is a halo group.

Thus, the Ni-thiolene catalyst complex can be any transition metal bis(1,2-enedithiolate). The Ni-thiolene catalyst complex is preferably a substituted 1,2-enedithiolate where the substituent is an aryl or alkyl group, more preferably the alkyl group is a halo-alkyl group, and most preferably the compound is the bis(dithiobenzil) metal compound or the bis[1,2-bis(trifluoromethyl)ethylene-1,2-dithiolato] metal compound.

The activating cocatalyst may be selected from the group consisting of alkylaluminoxanes, aluminum alkyls, aluminum halides, alkyl aluminum halides, Lewis acids, alkylating agents, and mixtures thereof. Preferably, the activating cocatalyst is methylaluminoxane.

The Ni-thiolene catalyst complexes described above may also be supported. The support material is preferably a porous material which includes, but is not limited to, inorganic oxides, talc, and inorganic chlorides. The support material may also be resinous materials such as polystyrene polyolefin or polymeric compounds. The support material may also be any other organic material that has an average particle size greater than approximately 10 micron. These catalysts are generally physisorbed on the support. The catalysts can also be supported on mesoporous materials. In a more preferred embodiment, the composition is supported by silica.

The method taught herein utilizing Ni-thiolene catalyst complexes advantageously couples α-olefin with ethylene that may contain contaminants. Hence, the coupling proceeds with non-pure α-olefin feeds. Such contaminants include $H_2$, CO, paraffins, $C_2H_2$, $H_2O$, $CO_2$, alkynes, and sulfur-containing compounds, such as $H_2S$, mercaptans, sulfides, thiopenes and derivatives thereof.

Shell Higher Olefin Process (SHOP) Catalysts:

Catalysts used in this process are neutral nickel (II) complexes bearing bidentate monoanionic ligands. The nickel catalysts are typically prepared in situ from a nickel salt, e.g. nickel chloride, and a chelating phosphorus oxygen ligand like o-diphenylphosphinobenzoic acid. Catalysts which have been described as useful as SHOP type catalysts are described in U.S. Pat. Nos. 3,635,937, 3,637,636, 3,676, 523 and 4,528,416, all incorporated by reference herein. Catalyst have also appeared in Peukert, M. et.al. Organometallics 1983, 2, 594, Keim, W. et.al. J. Organomet. Chem. 1983, 25I, 377, Keim, W. Angew. Chem. Int. Ed. Engl. 1983, 22, 503 (incorporated herein by reference), are also useful in the process according to the present invention.

The process according to the present invention utilizes ethylene in admixture with single or mixed linear α-olefin feeds or inexpensive mixed isomer feeds, such as butene raffinates that comprises between about 15 to about 25% 1-butene. The present invention is further described in the following non-limiting examples.

EXAMPLE 1

Preparation 1,1'bis(1-hydrobenzimidazol-2yl) methane (HBBIM)

1,1'bis(1-hydrobenzimidazol-2yl)methane (HBBIM) was prepared by the procedure reported in the literature [Vyas, P., C.; Oza, C., K.; Goyal, A., K. Chem. and Ind. 1980, 287–288]. The product was recrystallized from acetone/ ethanol mixture. $C_{15}H_{12}N_4$, FW=248.29; mp 331° C. (decomp.) $^1$H NMR ($CD_3SO_2CD_3$) δ 7.53(q, J=3.1 Hz, 4H), 7.16(q, J=3.1 Hz, 4H), 4.54(s, 2H), 2.51(s, 2H), $^{13}$C NMR ($CD_3SO_2CD_3$) δ 150.6, 139.1, 121.9, 115.1, 29.7. Rf=0.28 (Etoac).

EXAMPLE 2

Preparation of 1,1'bis(1-butylbenzimidazol-2yl) pentane,(tributBBIM)

A 2.00 g (8.06 mmol) quantity of HBBIM (product of Example 1) was dissolved in ca. 20 mL of dry DMSO under Ar. Then 2.0 g of NaH (80% dispersion in mineral oil) was added slowly under a positive flow of Ar and allowed to stir for an additional hour. Then 2.60 mL (24.2 mmol) of 1-bromobutane was added dropwise. The mixture was stirred at room temperature for one hr followed by an additional 1 hr at 40° C. Upon cooling the reaction was quenched with water and then further diluted with 400 mL of water to give a sticky solid which was collected by filtration and washed repeatedly with water and dried in a vacuum-oven, then recrystallized from a mixture of cyclohexane and acetone. $C_{27}H_{36}N_4$, FW=416.61; mp 82–83° C. $^1$H NMR ($CDC_{13}$) δ 7.79(m, 2H), 7.24(m, 6H), 4.88(t, J=7.9 Hz, 1H), 4.16(dsep, J=5.0 Hz, J=40.9 Hz, 4H), 2.59(m, 2H), 1.44(m, 4H), 1.16(m, 4H), 1.10(m, 2H), 0.99(m, 2H), 0.89(t, J=6.8 Hz, 3H), 0.61(t, J=7.0 Hz, 6H). $^{13}$C NMR ($CDCl_3$) δ

151.8, 142.4, 135.6, 122.6, 122.0, 119.6, 109.7, 44.0, 40.9, 31.5, 31.2, 30.1, 22.5, 20.0, 14.0, 13.4. Rf=0.73 (EtOAc).

EXAMPLE 3

Catalyst Synthesis: [1,1'bis(1-butylbenzimidazol-2yl)pentane]nickel(II) dichloride [Ni(tributBBIM)Cl$_2$]

A 100 mg (0.42 mmol) quantity of NiCl2.6H$_2$O was dissolved in 20 mL of absolute ethanol to give a yellow-green solution. Then 190 mg (0.46 mmol) of tributBBIM was added followed by the addition of 1 mL of triethyl orthoformate. The solution was heated to gentle reflux for ca. 5 min. Upon cooling violet dichroic blades formed and 227 mg of solid was collected by filtration and washed with triethylformate followed by pentane. (98%), C$_{27}$H$_{36}$C$_{12}$N$_4$Ni, FW=546.22; mp 324–325° C. (decomp.); X-ray crystallographic data: monoclinic, P2(1), a=14.0690 Å, b=14.1050 Å, c=14.3130 Å, α=90°, β=97.220°, γ=90°, V=2817.80.

EXAMPLE 4

Coupling Reaction of 1-Pentene with Ethylene Using Ni(tributylBBIM)Cl$_2$ Catalyst A glass lined Parr reactor was loaded in an argon-filled glove box, with [1,1'bis(1-butylbenzimidazol-2yl)pentane] nickel(II) dichloride [Ni(tributBBIM)Cl$_2$] complex (86 mg, FW 546.22, 1.57×10$^{-2}$ mmoles) (product of Example 3) followed by the addition of 2.05 g of 30% MAO solution in toluene (Al/Ni=673) and the Parr reactor was taken to a hood containing the controller for the reactor. In the addition vessel 12.12 g 1-pentene and 0.653 g ethylene (mole ratio of pentene to ethylene=7.42) was weighed. The reactor solution was stirred (stirring rate 500 RPM) at 25° C. and the contents of the addition vessel was added to the reactor. The mixture was stirred for 30 minutes at room temperature. The product was analyzed by gas chromatography-mass spectrometry. GC analysis of the product showed peaks due to heptenes along with peaks due to butenes and hexenes. The mole ratio of heptenes to butenes was 2.8.

EXAMPLE 5

Coupling Reaction of 1-Pentene with Ethylene Using Ni(tributylBBIM)Cl$_2$ Catalyst A glass lined Parr reactor was loaded in an argon-filled glove box, with [1,1'bis(1-butylbenzimidazol-2yl)pentane] nickel(II) dichloride [Ni(tibutBBIM)Cl$_2$] complex (83 mg, FW 546.22, 1.51×10$^{-2}$ mmoles) (product of Example 3) followed by 2.044 g of 30% MAO solution in toluene (Al/Ni=696) and the Parr reactor was taken to a hood containing the controller for the reactor. In the addition vessel 12.10 g 1-pentene and 0.241 g ethylene (mole ratio of pentene to ethylene=20.1) was weighed. The reactor solution was stirred (stirring rate 500 RPM) at 25° C. and the contents of additional vessel was added to the reactor. The mixture was stirred for 30 minutes at room temperature. The product was analyzed by gas chromatography-mass spectrometry. GC analysis of the product shows peaks due to heptenes along with peaks due to butenes and hexenes. The mole ratio of heptenes to butenes was 6.0.

EXAMPLE 6

Coupling Reaction of 1-Pentene with Ethylene Using Ni(tributylBBIM)Cl$_2$ Catalyst A glass lined Parr reactor was loaded in an argon-filled glove box, with [1,1'bis(1-butylbenzimidazol-2yl)pentane] nickel(II) dichloride [Ni(tributBBIM)Cl$_2$] complex (85 mg, FW 546.22, 1.55×10$^{-2}$ mmoles) (product of Example 3) followed by 2.05 g of 30% MAO solution in toluene (Al/Ni=696) and the Parr reactor was taken to a hood containing the controller for the reactor. In an addition vessel 12.35 g 1-pentene and 0.097 g ethylene (mole ratio of pentene to ethylene=51) was weighed. The reactor solution was stirred (stirring rate 500 RPM) at 25° C. and the contents of additional vessel was added to the reactor. The mixture was stirred for 30 minutes at room temperature. The product was analyzed by gas chromatography-mass spectrometry. GC analysis of the product shows peaks due to heptenes along with peaks due to butenes and hexenes. The mole ratio of heptenes to butenes was 10.2.

EXAMPLE 7

Synthesis of 2,6-bis[(2-methylphenylimino)methyl] methyl Pyridine

The ligand was synthesized following the literature method of Britovvsek G. J. P. et al. (Chem. Eur. J. 2000, 6, 2221), which is incorporated herein by reference. o-Toluidine (0.99 g, 9.25 mmol, 2.5 equiv) was added to a solution of 2,6-diformylpyridine (0.5 g, 3.7 mmol) in absolute ethanol (20 mL) at room temperature. The product precipitated immediately and the mixture was stirred at room temperature for 18 h. The product was filtered, washed with cold ethanol and dried in a vacuum oven (50° C.) overnight. Yield 67.4%. $^1$H NMR (CDCl$_3$); δ=8.58 (s, 2H; N=CH), 8.34 (d, 2H; pyrH$^3$), 8.31 (t, 1H; pyrH$^4$), 7.26–7.03 (m, 8H; ArH), 2.41 (s, 6H; ArCH$_3$). $^{13}$C NMR (CDCl$_3$); 159.34, 154.80, 149.84, 137.16, 132.37, 130.43, 126.84, 126.81, 126.55, 122.82, 117.50, 17.87 (ArCH$_3$). Mass spectrum (m/e): 313.

EXAMPLE 8

Synthesis of 2,6-bis[(2-methylphenylimino)methyl] methyl Pyridyliron(II) Chloride The complex was synthesized following the literature method of Britovvsek G. J. P. et al. (Chem. Eur. J. 2000, 6, 2221). FeCl$_2$ (0.1282 g, 1.01 mmol) was dissolved in hot n-butanol (20 mL) at 80° C. A suspension of 2,6-bis[(2-methylphenylimino)methyl]methyl pyridine (0.317 g, 1.08 mmol) in n-butanol was added dropwise at 80° C. The reaction mixture turned dark blue. After stirring at 80° C. for 30 min, the reaction mixture was allowed to cool to room temperature and stirred overnight. The reaction volume was reduced to 3 mL and diethyl ether was added to precipitate the product, which was subsequently washed three times with diethyl ether and dried in vacuum oven. Yield: 100%.

EXAMPLE 9

Coupling Reaction of 1-Pentene with Ethylene Using 2,6-bis[(2-methylphenylimino)methyl]methyl Pyridyliron(II) Chloride Catalyst A glass lined Parr reactor was loaded in an argon-filled glove box, 2,6-bis[(2-methylphenylimino)methyl]methyl pyridyliron(II) chloride complex (63 mg, FW 341.43, 1.84× 10$^{-2}$ mmoles) (product of Example 8) followed by 2.01 g of 30% MAO solution in toluene (Al/Fe=564) and the Parr reactor was taken to a hood containing the controller for the reactor. In an addition vessel 12.155 g 1-pentene and 0.447 g ethylene (mole ratio of pentene to ethylene=10.9) was weighed. The reactor solution was stirred (stirring rate 500

RPM) at 25° C. and the contents of additional vessel was added to the reactor. The mixture was stirred for 30 minutes at room temperature. The product was analyzed by gas chromatography-mass spectrometry. GC analysis of the product shows peaks due to heptenes along with peaks due to butenes and hexenes. The mole ratio of heptenes to butenes was 4.2.

EXAMPLE 10

Coupling Reaction of 1-Pentene with Ethylene Using 2,6-bis[(2-methylphenylimino)methyl]methyl Pyridyliron(II) Chloride Catalyst A glass lined Parr reactor was loaded in an argon-filled glove box, 2,6-bis[(2-methylphenylimino)methyl]methyl pyridyliron(II) chloride complex (60 mg, FW 341.43, 1.75× $10^{-2}$ mmoles) (product of Example 8) followed by 2.00 g of 30% MAO solution in toluene (Al/Fe=590) and the Parr reactor was taken to a hood containing the controller for the reactor. In an addition vessel 12.211 g 1-pentene and 0.143 g ethylene (mole ratio of pentene to ethylene=34.2) was weighed. The reactor solution was stirred (stirring rate 500 RPM) at 25° C. and the contents of additional vessel was added to the reactor. The mixture was stirred for 30 minutes at room temperature. The product was analyzed by gas chromatography-mass spectrometry. GC analysis of the product shows peaks due to heptenes along with peaks due to butenes and hexenes. The mole ratio of heptenes to butenes was 13.

EXAMPLE 11

Synthesis of Bis(dithiobenzil) Nickel [Ni(S$_2$C$_2$Ph$_2$)$_2$] Complex

The complex was synthesized following the literature method of Schrauzer and Mayweg (J. Am. Chem. Soc. 1965, 87, 1483). Benzoin (10 g) was reflux with 15 g of $P_4S_{10}$ in 70 ml of dioxane for 2 h. During this time the thiophosphoric esters of dithiobenzoin are formed and hydrogen sulfide is evolved. To the cooled and filtered reaction solution 5 g of NiCl$_2$.6H$_2$O in 20 ml of water was added and the reaction mixture was heated on a steam bath for 2 h. Black crystals of the complex are formed and collected by filtration. Yield 4.5 g (35% based on benzoin), mp 292° C. dec. UV-Vis (chloroform); 866, 602, 417, 377, 316, 270 nm.

EXAMPLE 12

Coupling Reaction of 1-Pentene with Ethylene Bis (dithiobenzil) Nickel [Ni(S$_2$C$_2$Ph$_2$)$_2$]

A glass lined Parr reactor was loaded in an argon-filled glove box, Bis(dithiobenzil) Nickel [Ni(S$_2$C$_2$Ph$_2$)$_2$ complex (86 mg, FW 542, 1.58×$10^{-2}$ mmoles) (product of Example 11) followed by 2.012 g of 30% MAO solution in toluene (Al/Ni=656) and the Parr reactor was taken to a hood containing the controller for the reactor. In an addition vessel 12.197 g 1-pentene and 0.438 g ethylene (mole ratio of pentene to ethylene=11.14) was weighed. The reactor solution was stirred (stirring rate 500 RPM) at 25° C. and the contents of additional vessel was added to the reactor. The mixture was stirred for 30 minutes at room temperature. The product was analyzed by gas chromatography-mass spectrometry. GC analysis of the product shows peaks due to heptenes along with peaks due to butenes and hexenes. The mole ratio of heptenes to butenes was 3.6.

EXAMPLE 13

Coupling Reaction of 1-Pentene with Ethylene Using 2,6-bis[(2-methylphenylimino)methyl]methyl Pyridyliron(II) Chloride Catalyst A glass lined Parr reactor was loaded in an argon-filled glove box, 2,6-bis[(2-methylphenylimino)methyl]methyl pyridyliron(II) chloride complex (6.8 mg, FW 398.12, 1.71× $10^{-2}$ mmoles) (product of Example 8) followed by 2.025 g of 30% MAO solution in toluene was added (Al/Fe=526) and the Parr reactor was taken to a hood containing the controller for the reactor. In the addition vessel 12.178 g 1-pentene and 0.08 g ethylene (mole ratio of pentene to ethylene=61 to 1) was weighed. The reactor solution was stirred (stirring rate 500 RPM) at 25° C. and the contents of additional funnel was added to the reactor. The mixture was stirred for 30 minutes at room temperature. The product was analyzed by gas chromatography-mass spectrometry. GC analysis of the product shows peaks due to heptenes along with peaks due to butenes and hexenes. The mole ratio of heptenes to butenes was 24 to 1.

EXAMPLE 14

Synthesis of 2,6-bis(phenylimino)methyl) Pyridine 2,6-pyridine dicarboxaldehyde (0.3071 g, 2.3 mmol) was added to a solution of aniline (0.5292 g, 5.7 mmol) in absolute ethanol (20 mL) at room temperature. 0.5 mL of formic acid was then added to the above solution. The mixture was stirred at room temperature for 65 h. The product was filtered, washed with cold ethanol and dried in a vacuum oven (50° C.) overnight yielding 0.2245 g (34.2%).

EXAMPLE 15

Synthesis of 2,6-bis (Phenylimino) Pyridyliron(II) Chloride

FeCl₂ ⟶

FeCl$_2$ (0.0666 g, 0.5 mmol) was dissolved in hot n-butanol (20 mL) at 80° C. A suspension of 2,6-bis (phenylimino) pyridine (0.15 g, 0.5 mmol) in n-butanol was added dropwise at 80° C. After stirring at 80° C. for 30 min, the reaction mixture was allowed to cool to room temperature and stirred overnight. The reaction volume was reduced to a 3 mL and diethyl ether was added to precipitate the product, which was subsequently washed three times with diethyl ether and dried in vacuum oven. Yield: 0.170 g (87.5%).

EXAMPLE 16

Coupling Reaction of 1-Pentene with Ethylene Using 2,6-bis (Phenylimino) Pyridyliron(II) Chloride A glass lined Parr reactor was loaded in an argon-filled glove box, 2,6-bis (phenylimino) pyridyliron(II) chloride complex (6.5 mg, FW 370.07, $1.76 \times 10^{-2}$ mmoles) (product of Example 15) in 1.03 g of dichloromethane, followed by 2.068 g of 30% MAO solution in toluene was added (Al/Fe=609) and the Parr reactor was taken to a hood containing the controller for the reactor. In the addition vessel 12.173 g 1-pentene and 0.414 g ethylene (mole ratio of pentene to ethylene=11.8) was weighed. The reactor solution was stirred (stirring rate 500 RPM) at 25° C. and the contents of additional funnel was added to the reactor. The mixture was stirred for 30 minutes at room temperature. The product was analyzed by gas chromatography-mass spectrometry. GC analysis of the product shows peaks due to heptenes along with peaks due to butenes and hexenes. The mole ratio of heptenes to butenes was 1.3.

EXAMPLE 17

Coupling Reaction of 1-Pentene with Ethylene Using 2,6-bis (Phenylimino) Pyridyliron(II) Chloride A glass lined Parr reactor was loaded in an argon-filled glove box, 2,6-bis (phenylimino) pyridyliron(II) chloride complex (7.2 mg, FW 370.07, $1.95 \times 10^{-2}$ mmoles) (product of Example 15) in 1.07 g of dichloromethane, followed by 2.0044 g of 30% MAO solution in toluene was added (Al/Fe=533) and the Parr reactor was taken to a hood containing the controller for the reactor. In the addition vessel 12.294 g 1-pentene and 0.159 g ethylene (mole ratio of pentene to ethylene=30) was weighed. The reactor solution was stirred (stirring rate 500 RPM) at 25° C. and the contents of additional funnel was added to the reactor. The mixture was stirred for 30 minutes at room temperature. The product was analyzed by gas chromatography-mass spectrometry. GC analysis of the product shows peaks due to heptenes along with peaks due to butenes and hexenes. The mole ratio of heptenes to butenes was 2.4.

EXAMPLE 18

Coupling Reaction of 1-Pentene with Ethylene Using 2,6-bis (Phenylimino) Pyridyliron(II) Chloride A glass lined Parr reactor was loaded in an argon-filled glove box, 2,6-bis (phenylimino) pyridyliron(II) chloride complex (6.8 mg, FW 370.07, $1.84 \times 10^{-2}$ mmoles) (product of Example 15) in 1.03 g of dichloromethane, followed by 2.0103 g of 30% MAO solution in toluene was added (Al/Fe=566) and the Parr reactor was taken to a hood containing the controller for the reactor. In the addition vessel 12.263 g 1-pentene and 0.103 g ethylene (mole ratio of pentene to ethylene=48 to 1) was weighed. The reactor solution was stirred (stirring rate 500 RPM) at 25° C. and the contents of additional funnel was added to the reactor. The mixture was stirred for 30 minutes at room temperature. The product was analyzed by gas chromatography-mass spectrometry. GC analysis of the product shows peaks due to heptenes along with peaks due to butenes and hexenes. The mole ratio of heptenes to butenes was 3.6.

EXAMPLE 19

Synthesis of 2,6-bis[1-(2-methylphenylimino)ethyl] Pyridine

The ligand was synthesized following the literature method of Britovvsek G. J. P. et al. (*Chem. Eur. J.* 2000, 6, 2221). O-Toluidine (19.70 g, 0.1838 mol) was added to a solution of 2,6-acetylpyridine (3 g, 0.01838 mol) in methanol (30 mL) at room temperature. 1-mL formic acid was then added to the above solution. The solution was refluxed for 72 h and cooled in the freezer for 24 h. The product was filtered and dried in a vacuum oven (50° C.) overnight. Yield 21%. Mass spectrum (m/e): 341.

EXAMPLE 20

Synthesis of 2,6-bis[1-(2-methylphenylimino)ethyl] Pyridyliron(II) Chloride

+

-continued

FeCl$_2$ →

The complex was synthesized following the literature method of Britovvsek G. J. P. et al. (*Chem. Eur. J.* 2000, 6, 2221). FeCl$_2$ (0.1856 g, 1.46 mmol) was dissolved in hot n-butanol (30 mL) at 80° C. A suspension of 2,6-bis[1-(2-methylphenylimino)ethyl] pyridine (0.5 g, 1.46 mmol) in n-butanol was added dropwise at 80° C. After stirring at 80° C. for 30 min, the reaction mixture was allowed to cool to room temperature and stirred overnight. The reaction volume was reduced to a 3 mL and diethyl ether was added to precipitate the product, which was subsequently washed three times with diethyl ether and dried in vacuum oven. Yield: 0.5762 g (84%).

EXAMPLE 21

Coupling Reaction of 1-Pentene with Ethylene Using 2,6-bis[1-(2-methylphenylimino)ethyl] Pyridyliron(II) Chloride Catalyst A glass lined Parr reactor was loaded in an argon-filled glove box, 2,6-bis[1-(2-methylphenylimino)ethyl] pyridyliron(II) chloride complex (7.6 mg, FW 468.19, 1.62× 10$^{-2}$ mmoles) (product of Example 20) followed by 2.07 g of 30% MAO solution in toluene was added (Al/Fe=660) and the Parr reactor was taken to a hood containing the controller for the reactor. In the addition vessel 12.072 g 1-pentene and 0.432 g ethylene (mole ratio of pentene to ethylene=11.2 to 1) was weighed. The reactor solution was stirred (stirring rate 500 RPM) at 25° C. and the contents of additional funnel was added to the reactor. The mixture was stirred for 30 minutes at room temperature. The product was analyzed by gas chromatography-mass spectrometry. GC analysis of the product shows peaks due to heptenes along with peaks due to butenes and hexenes. The mole ratio of heptenes to butenes was 23.7.

EXAMPLE 22

Figure 1:
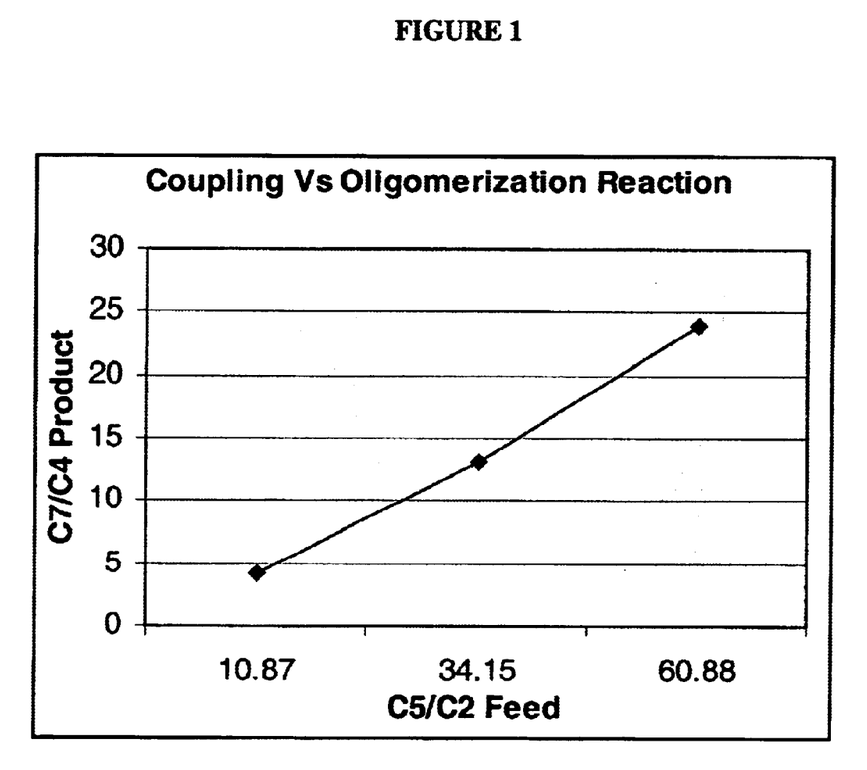
FIG. 1 is a graph plotting coupling versus oligomerization reaction for Examples 9, 10 and 13 for the purpose of demonstrating that as the feed ratio of 1-pentene to ethylene changes, the ratio of coupled product (C7) to ethylene dimerization product (C4) also changes.

If one compared the results from coupling Examples 9, 10 and 13, it is clear that as the feed ratio of 1-pentene to ethylene changes, the ratio of coupled product (C7) to ethylene dimerization product (C4), i.e., C7/C4 ratio also changes, as shown in FIG. 1, attached hereto.

EXAMPLE 23

Figure 2:
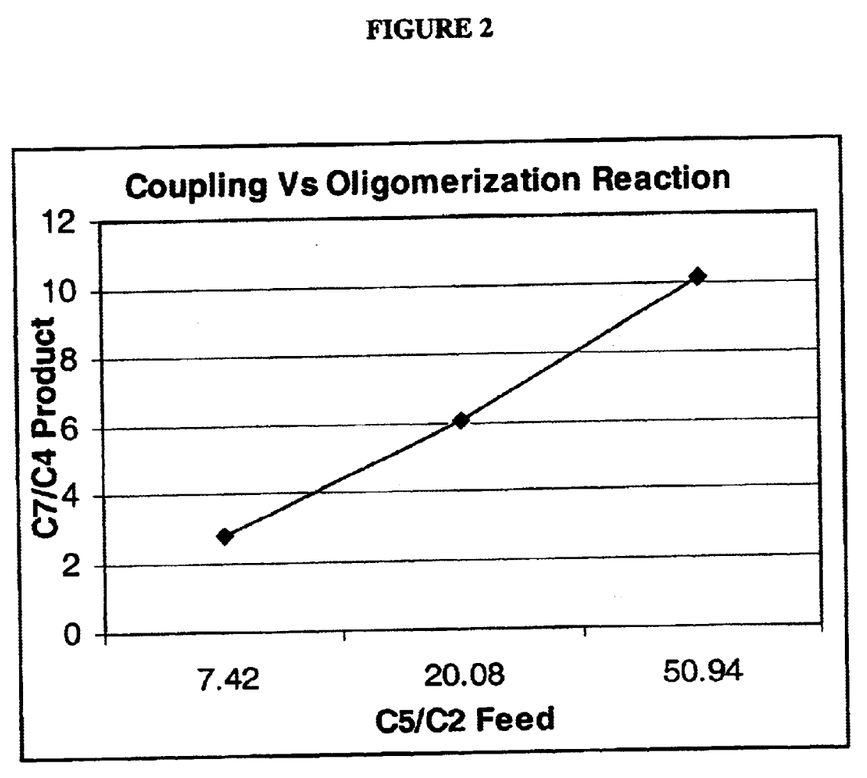
FIG. 2 is a graph plotting coupling versus oligomerization reaction for Examples 4, 5 and 6.

If one compare the results from coupling Examples 4, 5 and 6, it is clear that as the feed ratio of 1-pentene to ethylene changes, the ratio coupled product (C7) to ethylene dimerization product (C4), i.e., C7/C4 ratio also changes, as shown in FIG. 2.

EXAMPLE 24

Figure 3:
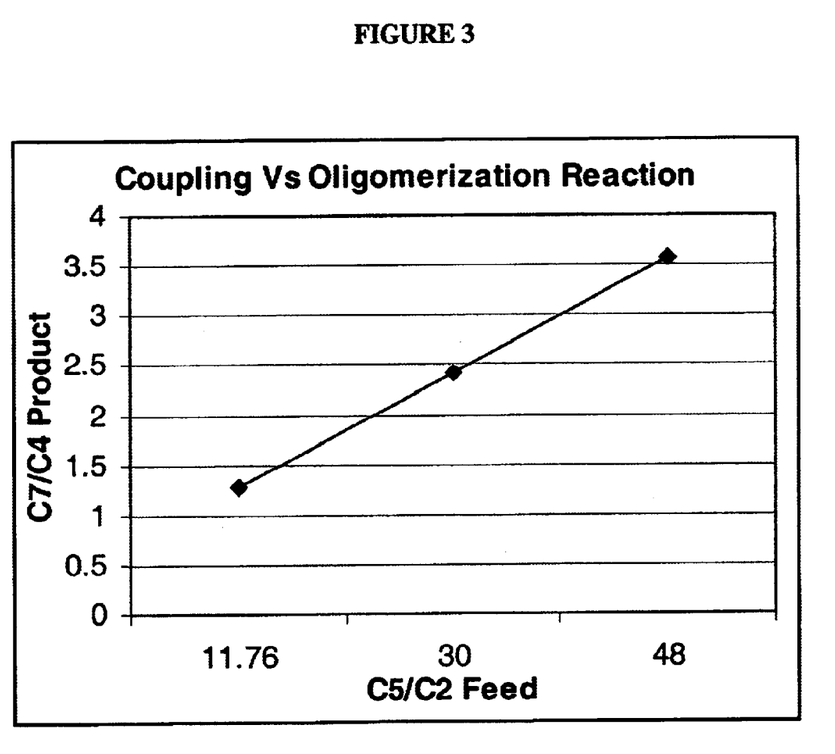
FIG. 3 is a graph plotting coupling versus oligomerization reaction for Examples 16, 17 and 18.

If one compare the results from coupling Examples 16, 17 and 18, it is clear that as the feed ratio of 1-pentene to ethylene changes, the ratio coupled product (C7) to ethylene dimerization product (C4), i.e., C7/C4 ratio also changes, as shown in FIG. 3.

These examples clearly demonstrate that conventional oligomerization catalysts can be used as effective coupling catalyst to make α-olefins. Some of the catalysts that can be used for coupling reaction include chromium trimerization catalyst, Brookhart type Ni and Pd catalysts, Fe catalysts, Ni-BBIM catalysts, Ni thiolene catalysts and SHOP catalysts. These catalyst complexes with activator can be supported on a porous carrier and such supported catalysts may be employed for coupling reactions. Preferred supports include alumina, silica, crosslinked polymers, ionic liquids, and mesoporous material like MCM-41.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A process for producing a linear α-olefin which comprises:
   reacting a feed comprising a stoichiometric excess of a terminal $C_n$ olefin with ethylene in the presence of a transition-metal based catalyst selected from the group consisting of chromium trimerization catalysts, metal (II) α-diimine complexes, pyridine bisimine iron or cobalt complexes, pseudotetrahedral nickel complexes, Ni-thiolene catalysts and neutral nickel (II) complexes bearing bidentrate monoanionic ligands to produce a $C_{n+2}$ linear α-olefin, wherein said catalyst exhibits a Schulz-Flory constant of less than about 0.8 as observed for ethylene oligomerization and wherein n is an integer between about 3 to 20.

2. The process according to claim 1, wherein said terminal olefin is at least one selected from the group consisting of: propylene, 1-butene, 1-pentene, 1-hexene, 1-heptene and 1-octene and mixtures thereof.

3. The process according to claim 1, wherein said linear α-olefin is selected from the group consisting of: $C_6$–$C_{10}$ linear α-olefins.

4. The process according to claim 1, wherein said reaction step is conducted at a temperature in the range from about −100 to about 250° C.

5. The process according to claim 1, wherein said temperature is in the range between about room temperature to about 100° C.

6. The process according to claim 1, wherein said reaction step is conducted at a pressure from about 0 to about 30,000 psig.

7. The process according to claim 1, wherein said pressure is in the range from about 0 to about 10,000 psig.

8. The process according to claim 1, wherein said pressure is in the range from about 5 to about 3,000 psig.

9. The process according to claim 1, wherein said terminal olefin to ethylene molar ratio is in the range between about 2:1 to about 1,000:1.

10. The process according to claim 1, wherein said terminal olefin to ethylene molar ratio is in the range between about 10:1 to about 100:1.

11. The process according to claim 1, wherein said reaction step is a catalytic coupling of said terminal olefin and said ethylene to form said linear α-olefin.

12. The process according to claim 1, wherein said reaction step is performed in the presence of a solvent.

13. The process according to claim 12, wherein said solvent is selected from the group consisting of: ethane, propane, butane, pentane, hexane, toluene, cyclohexane, cyclopentane, tetralin, methylene chloride, chlorobenzene, chloroform, o-dichlorobenzene, carbon dioxide and mixtures thereof.

14. The process according to claim 1 wherein said transition metal-based catalyst further comprises an activator.

15. The process according to claim 1 wherein said transition metal-based catalyst is a supported catalyst.

16. The process according to claim 15 wherein said supported catalyst is a silica supported catalyst.

17. The process according to claim 1, wherein said pseudotetrahedral nickel complexes have the formula LMX $(X')_n$ wherein n equals 0 or 1; X and X' are independently selected from the group consisting of halides, hydride, triflate, acetates, borates, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolates, carbon monoxide, cyanate, olefins, and any other moiety into which a monomer can insert; M is selected from the group consisting of nickel, palladium, and platinum and L is a nitrogen-containing monodentate, bidentate, tridentate or multidentate ligand with one or more nitrogen atoms.

18. The process according to claim 1, wherein said pyridine bisimine iron or cobalt complex is a Fe(II)-pyridine bisimine or Co(II)-pyridine bisimine complex having the formula where R1, R2, and R3 are each independently selected from the group consisting of hydrogen, halogen, hydrocarbyl, substituted hydrocarbyl, heterohydrocarbyl, and substituted heterohydrocarbyl.

19. The process according to claim 18 wherein said pyridine bisimine iron or cobalt complex is a Fe(II)-pyridine bisimine or Co(II)-pyridine bisimine complex is selected from the group consisting of 2,6-bis[1-(2-methylphenylimino)ethyl]pyridyliron (II) chloride: 2,6-bis[(2-methylphenylimino)methyl]pyridyliron(II)chloride; and mixtures thereof.

20. The process according to claim 1, wherein said metal (II) α-diimine complexes comprise a catalyst having the formula Where M is Ni or Pd and each R is independently selected from hydrogen, haologen, hydrocarbyl, substituted hydrocarbyl, heterohydrocarbyl and substituted heterohydrocarbyl.

21. The process of claim 1 wherein said Ni-thiolene catalyst is selected from the group of catalysts consisting of a catalyst having the formula $M[S_2C_2(R^aR^b)]_2$ $M[S_2C_6(R^1R^2R^3R^4)]_2$ wherein M is a transition metal selected from the group consisting of Fe, Co, Ni, Pd or Pt and $R^a$ and $R^b$ may be the same or different, and are independently selected from hydrogen, electron-withdrawing groups including those that are or contain heterocyclic, cyano, carboxylate, carboxylic ester, keto, nitro, and sulfonyl groups, and hydrocarbyl groups, including unsubstituted, fully, or partially substituted alkyl, cyclo alkyl, alkenyl and aryl groups.

22. The process of claim 21 wherein $R^a$ and $R^b$ are cyano groups, and halo substituted groups.

23. The process according to claim 1, wherein the process is either a continuous, semi-continuous or batch type process.

24. The process of claim 22 wherein said cyano groups are CN groups and said halo substituted groups are $CF_3$ groups.

* * * * *